United States Patent
Warthen et al.

(10) Patent No.: US 7,435,422 B2
(45) Date of Patent: Oct. 14, 2008

(54) NON-ANIMAL ORIGIN STABILIZERS AND PROCESSES FOR PRODUCING THE SAME

(75) Inventors: R. Monty Warthen, Salisbury, MD (US); Christopher P. Gully, Salisbury, MD (US)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 11/031,026

(22) Filed: Jan. 7, 2005

(65) Prior Publication Data

US 2005/0163803 A1 Jul. 28, 2005

Related U.S. Application Data

(60) Provisional application No. 60/537,455, filed on Jan. 15, 2004.

(51) Int. Cl.
 *A61K 39/10* (2006.01)
(52) U.S. Cl. .................................................. 424/253.1
(58) Field of Classification Search .................. None
 See application file for complete search history.

(56) References Cited

U.S. PATENT DOCUMENTS

| | | | | |
|---|---|---|---|---|
| 5,925,359 | A | * | 7/1999 | Van Woensel et al. .... 424/204.1 |
| 5,948,411 | A | | 9/1999 | Koyama |
| 6,039,958 | A | | 3/2000 | Koyama |
| 6,231,860 | B1 | | 5/2001 | Fanget |
| 6,258,362 | B1 | * | 7/2001 | Loudon et al. ........... 424/229.1 |
| 6,284,256 | B1 | * | 9/2001 | Savelkoul et al. ........ 424/253.1 |

FOREIGN PATENT DOCUMENTS

| | | |
|---|---|---|
| DE | 299213 | 4/1992 |
| GB | 1449606 | 9/1976 |
| WO | 9318790 | 9/1993 |
| WO | 9955348 | 11/1999 |

OTHER PUBLICATIONS

The term "about" Merriam-Webster online dictionary. see at the web at http://www.m-w.com. p. 1.*
Ferris, N. P. et al.: "Freeze-drying foot-and-mouth disease virus antigens. I. Infectivity studies" J. General Virological Methods, (1990) 29 pp. 43-52.
Thompson, D. J. et al. (May 2001). "Evaluation of an animal free Vegetable Peptone Phosphate Broth for productivity in tissue culture and fermentation applications" Abstracts of the General Meeting of the American Society for Microbiology, 101, pp. 549; XP-002338191.
International Search Report, Written Opinion and Preliminary Report on Patenability for PCT/US2005/000359, published as WO 2005/071067.

* cited by examiner

*Primary Examiner*—Irene Marx
*Assistant Examiner*—Satyendra K Singh
(74) *Attorney, Agent, or Firm*—William M. Blackstone; William P. Ramey, III

(57) ABSTRACT

Embodiments of the present invention generally comprise stabilizers for biological products that are free from animal origin excipients/components, such stabilizers functioning well in lyophilization procedures.

6 Claims, 3 Drawing Sheets

NON-ANIMAL ORIGIN STABILIZERS AND PROCESSES FOR PRODUCING THE SAME

RELATED APPLICATIONS

This application claims priority to U.S. provisional application 60/537,455 (filed on Jan. 15, 2004).

FIELD OF THE INVENTION

Various embodiments of the present invention generally comprise compositions and processes for increasing stability of biological substances.

BACKGROUND OF THE INVENTION

Vaccines are often referred to as biologicals or biological products. This is because they may be prepared by cultivation of live micro-organisms using live tissue cells of animal origin as a substrate. Moreover the culture media are often supplemented with specific substances of animal origin, notably serum, to achieve a satisfactory growth of the micro-organisms. Also in the production process itself, substances of animal origin are often used, such as in a stabilizer. Consequently there exists a potential risk that vaccines may become contaminated with extraneous "animal origin" agents.

Often, a vaccine is mixed with stabilizers, e.g. to protect degradation-prone components from being degraded, to enhance the shelf-life of the vaccine, or to improve freeze-drying efficiency. Useful stabilizers are i.a. SPGA (Bovarnik et al., 1950, J. Bacteriology, vol. 59, p. 509), skimmed milk, gelatine, bovine serum albumin, carbohydrates e.g. sorbitol, mannitol, trehalose, starch, sucrose, dextran or glucose, proteins such as albumin or casein or degradation products thereof, and buffers, such as alkali metal phosphates. These stabilizers are a source of "animal origin" agents/components.

The prior art has identified the need for the production of biological materials that are free from contamination, such as "animal origin" contamination. Biological materials are often subjected to numerous tests and/or evaluations to illustrate that the materials are free from contamination. Accordingly, production of a vaccine or immunogenic composition with a stabilizer containing animal origin components is, in itself, a source of contamination.

Such animal origin components often require extra precautions such as filter sterilization, and present difficulties, such as batch to batch variability of a vaccine, and the like. In fact, vaccines grown in a serum free culture are often mixed with stabilizers of animal origin, thereby producing a vaccine which is no longer free of animal origin components.

Accordingly, the art field desires stabilizer that is free from animal origin components. An animal origin free stabilizer would be sterilizable by autoclaving. An animal origin free stabilizer (a Non-Animal Origin (NAO) Stabilizer) would not suffer complicating batch to batch variability of animal compounds. However, and most importantly an animal origin free stabilizer would allow an animal origin free vaccine, as up to now serum-free culturing already reduced the risk of extraneous agents in the animal compounds, however those products were still freeze dried with compounds of animal origin, thereby re-introducing a risk of contamination.

Examples of prior art documents that show the state of the art prior to Applicants' invention comprise: WO 93/18790, and U.S. Pat. Nos. 5,948,411; 6,039,958; and, 6,258,362

SUMMARY OF THE INVENTION

Various embodiments of the present invention generally comprise compositions and processes for increasing the stability of biological substances. In an embodiment, the biological substance is stabilized during drying and/or freeze-drying, such as, and not by way of limitation, lyophilization. The dried compositions derived without using excipents from so-called "animal origin" components. In an embodiment, the invention comprises an alcohol, a sugar, and a buffer. In an alternate embodiment, the sugar is a carbohydrate.

Embodiments of these formulations can be used in stabilization of cell lines, viruses (live/attenuated/vectored/and/or recombinant), bacteria (live/attenuated/vectored/viral proteins and/or recombinant), bacterial or viral components (toxins, proteins), fungi, plasmids (all iso-forms) and viral delivered vectors generated from cell culture, and/or other proteins, including, but not limited to, recombinant proteins.

Further, various embodiments of this formulation can apply to human, feline, animal component, equine, porcine, bovine, ovine, aquaculture, and/or any other specie's vaccines and/or the stabilization thereof.

This summary is not intended to act as a limitation on the scope of the appended claims. For a further understanding of the invention, attention should be had on the following detailed description, examples, and appended claims.

DETAILED DESCRIPTION OF THE INVENTION

Figure 1:
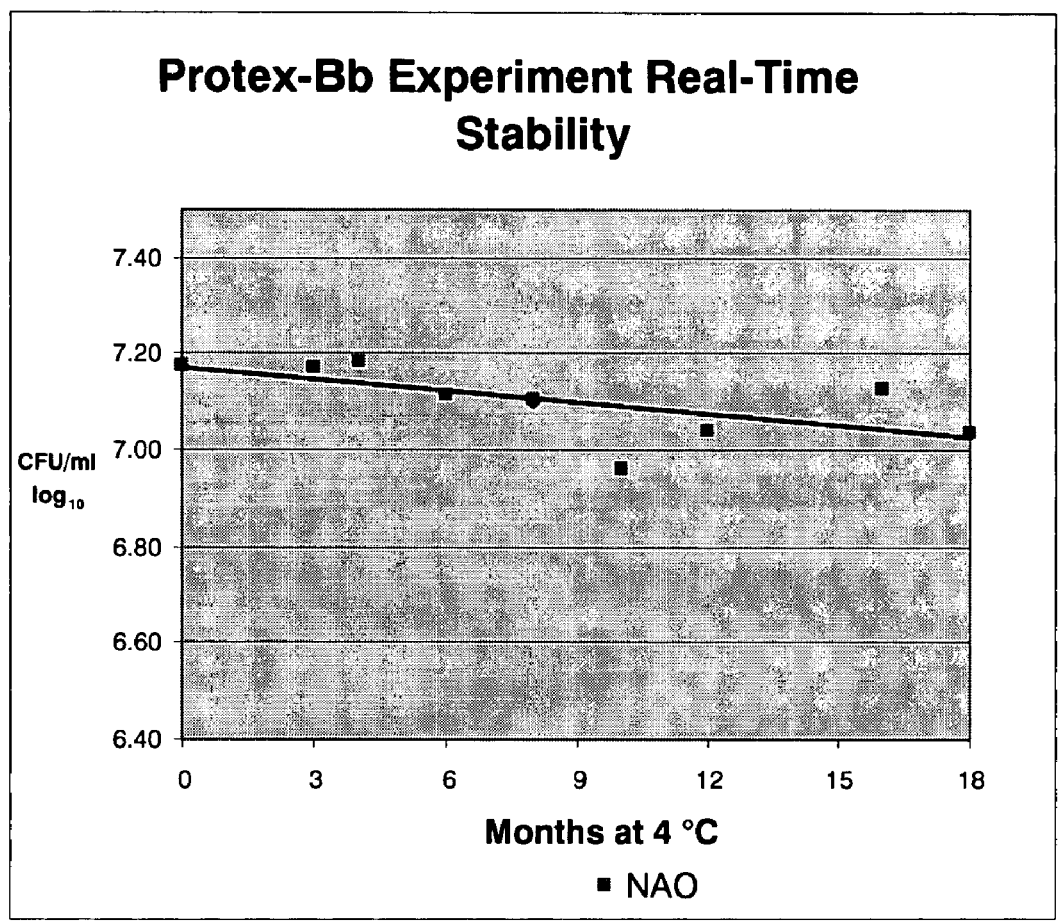
FIG. 1 is an illustration of a lyophilization study of an NAO stabilized vaccine compared to an animal origin component stabilized vaccine titrated over the course of 18 months.

As used herein, the term "lyophilize," and conjugations thereof, means and refers to, to dry, freeze dry. As used herein, the term "animal origin" means and refers to originating from animals. Likewise, the term "non-animal origin" means and refers to not originating directly or indirectly from animals.

As used herein, the term "stabilize," and conjugations thereof, means and refers to make or hold stable, firm, steadfast and to maintain at about a given or substantially unfluctuating level, about a given or substantially unfluctuating quality and about a given or substantially unfluctuating quantity. However, it is understood that some fluctuation in the level, quality, and/or quantity of the stabilized composition may be encountered. Embodiments of the present invention are intended to encompass stabilizers that allow such fluctuations. As well, stabilizers are oftern referred to or used as a dry stabilizer, a bulk stabilizer, a cryoprotectant, a thermo-stabilizer, an osmoprotectant, a desiccation protectant, and the like. Such terms are specifically meant to be included within the stabilizers of the present invention.

As used herein, the term "protein" means and refers to a molecular chain of amino acids. A protein is not of a specific length and can, if required, be modified in vivo or in vitro, by, e.g. glycosylation, amidation, carboxylation or phosphorylation. Inter alia, peptides, oligopeptides and polypeptides are included within the definition. A protein or peptide can be of biologic and/or synthetic origin.

As used herein, the term "nucleic acid" means and refers to a molecular chain of desoxy- or ribonucleic acids. A nucleic acid is not of a specific length, therefore polynucleotides, genes, open reading frames (ORF's), probes, primers, linkers, spacers and adaptors are included within the definition. A nucleic acid can be of biologic and/or synthetic origin. The nucleic acid may be in single stranded or double stranded form. The single strand may be in sense or anti-sense orientation. Also included within the definition are modified RNAs or DNAs. Modifications in the bases of the nucleic acid may be made, and bases such as Inosine may be incorporated. Other modifications may involve, for example, modifications of the backbone.

As used herein, a pharmaceutically acceptable carrier is understood to be a compound that does not adversely affect the health of the animal or organism to be vaccinated, at least not to the extent that the adverse effect is worse than the effects seen when the animal is not vaccinated. A pharmaceutically acceptable carrier can be e.g. sterile water or a sterile physiological salt solution. In a more complex form the carrier can e.g. be a buffer.

As used herein, the term "carbohydrate" means and refers to the four major groups of saccharides: mono-, di-, oligo-, and poly-saccharides.

Various embodiments of the present invention generally comprise compositions and processes for increasing the stability of biological substances. In an embodiment, the biological substance is stabilized during drying and/or freeze-drying, such as, and not by way of limitation, lyophilization and subsequent storage. The dried compositions derived without using excipients from so-called "animal origin" components. In an embodiment, the invention comprises an alcohol, a sugar, and a buffer. In an alternate embodiment, the sugar is a carbohydrate.

Compositions of the invention include examples free from protein (other than any protein forming part of the biological substance being stabilized), in particular free from gelatin or other animal protein or its hydrolysate, such as, but not limited to, acid hydrolysate or enzyme hydrolysate, or other material of animal origin.

Embodiments of these formulations can be used in stabilization of cell lines, viruses (live/attenuated/vectored/viral proteins and/or recombinant), bacteria (live/attenuated/vectored/ and/or recombinant), bacterial components (toxins, proteins), fungi, plasmids (all iso-forms) and viral delivered vectors generated from cell culture and the like. In an embodiment, the present invention generally comprises a polyhydroxyl alcohol (polyalditol), soybean peptone and dextran in combination with a poly- and/or mono-saccharide and a buffer. In various other embodiments, the present invention consists essentially of a polyhydroxy alcohol, soybean peptone and dextran in combination with a poly- and/or mono-saccharide and a buffer.

Further, various embodiments of this formulation can apply to vaccines, such as human, feline, equine, porcine, bovine, ovine, aquaculture, and/or any other species' vaccines and/or the stabilization thereof.

In an embodiment according to the present invention, there is provided a stabilizing composition comprising a non-animal origin peptone; a buffer; and a saccharide and/or a polyalditol, and/or an other mono- or oligo-saccharide or derivative thereof. The composition may also comprise dextran or other polysaccharide. Optional further ingredients can include further amino acid(s), e.g. diacidic amino acid(s) such as sodium L-glutamate or L-aspartate, or a mixture of amino acids. Among further ingredients that can be suitable are those referred to in the prior art documents mentioned above, very preferably those of vegetable, bacterial and/or mineral origin.

In certain other embodiments, the stabilized compositions can comprise (i) a polysaccharide with a molecular weight above about 5000, preferably about 100,000 to about 180,000. In another embodiment, the polysaccharide has a molecular weight less than about 800,000 e.g., for example, dextran, (ii) a source of mixed amino acids and peptides of non-animal origin, such as vegetable or bacterial origin, e.g. vegetable peptone, e.g. peptone made by enzymic or acid hydrolysis of soybean protein and/or the like (iii) buffer, such as tris-HCl, bicarbonate, phosphate, citrate, and/or the like and (iv) saccharide or sugar alcohol, such as lactose, sucrose, sorbitol, and/or the like. Additionally, compositions of the present invention can further comprise additional ingredients, such as further amino acids, and/or mixtures of amino acids.

Embodiments of the present invention have demonstrated good retention of titre after storage. In an embodiment, the stabilized composition may be stored for a period of time up to eighteen (18) months. In an alternate embodiment, the stabilized composition may be stored for a period of time up to thirty-six (36) months. Further, in yet another alternate embodiment, the stabilized composition may be stored for a period of time up to sixty (60) months. Various other embodiments of the present invention contemplate formulation of a stabilized composition for varying storage times/periods, as required by the application.

A further aspect of the invention concerns the use of vegetable peptone or other mixed amino acids of vegetable or bacterial origin, free of animal protein or animal protein hydrolysate, or other material of animal origin, in compositions for stabilising virus, and in the manufacture of dried stabilised virus compositions for vaccine and other uses as mentioned herein.

Suitable vegetable peptones comprise, but are not limited to, a preparation made from clean edible solvent-extracted soya flour by hydrolytic digestion with protease, to give a product with an average molecular weight in the range about 300-400 and substantially free from higher m.w. constituents above about m.w. 2000. Soluble carbohydrate of vegetable origin can also be present in such a peptone preparation. Alternatively, mixed aminoacids of vegetable or bacterial origin can be used in place of peptone as described above.

Various embodiments generally comprise a vaccine virus. It has been found that the stabilizing compositions or the present invention are well suited for stabilizing a vaccine virus or bacteria during and after lyophilisation and subsequent storage. Lyophilization may be performed as is common in the art. In a particular example, and not by way of limitation, a lyophilization run may be from about 1 to about 14 days at a temperature range of from about −50.0° C. to about 40° C. In an embodiment, the period of lyophilization is about 31 hours. In another embodiment, the period of lyophilization is from about 24 hours to about 120 hours. In another embodiment, the period of lyophilization is about 20 hours to about 240 hours.

An exemplary lyophilization may comprise the components and steps of freezing vials, containing product including stabilizer, 2-24 hours, at −20° C. to −60° C. (or even lower temperatures) on shelves of a lyophilizer (freeze-drier or the like); at a vacuum of 10 to 300 microns; a minimum temperature of the lyophilized product is commonly about −10° C. while in primary drying, most typically −25° C., but not greater that −100° C. The time involved in primary drying can range from minutes to days.

Typically, but not always, after primary drying is complete, the product is temperature is raised through secondary drying to a maximum temperature of about 76° C. and the maximum time of about 96 hours (However, the number of hours and/or temperature may vary, as would be dependent upon the product). In an embodiment, upon completion of secondary drying, the product is held at 4° C. in the final containers and the stoppers are seated under vacuum. However, the final temperature may vary, as is common in the art.

Typically, vials are tested for residual moisture. The optimal moisture range is between about 1% and about 10%, most preferably about 3%. The range of total lyophilization time (including freezing) is 1-720 hours for a 3 ml vial filled with 0.5 ml of product containing about 1 to about 80% stabilizer.

As well, embodiments of the present invention further comprise processes for producing a stabilized composition with a vaccine virus strain comprising the steps of mixing (i) a vaccine virus strain, (ii) an alcohol, (iii) a sugar, and (iv) a buffer, wherein the vaccine contains no animal origin components. In another embodiment, the composition further comprises a vegetable peptone. The composition can optionally further comprise (v) dextran or another polysaccharide.

The lyophilisation of the product can be carried out over any suitable period according to conventional lyophilisation practice, such as at a temperature below the glass transition temperature of the frozen liquid to be lyophilised, and the product can be in the form of a solid dried cake within a glass vial, perferably under sterile conditions.

The product can be rehydrated at convenience with sterile aqueous liquid, such as water for injection.

Examples of the vaccine virus or bacterial strains suitable for embodiments of the present invention comprise any virus or bacterial strain.

It has been found that the compositions have improved or are at least equivalent in stability and are from non-animal origin/derived sources making the regulatory aspects of producing said vaccine(s) more efficient and potentially more safe with less reactivity. These stabilizers comprise a polyhydroxy alcohol, buffer(s), mono- or poly-saccharides and/or a plant derived peptone, such as soybean peptone and its equivalents.

In an embodiment, the loss of titer from lyophilization is less than about 0.4 log. In an alternate embodiment, the loss of titer is less than about 0.2 log. In an alternate embodiment, the loss in titer from lyophilization is about 0.0 log. However, the actual loss in titer will vary from antigen to antigen, but the Non Animal Origin Stabilizers of the present invention have shown general applicability to minimize titer loss with all vaccine antigens.

EXAMPLES

Example 1

In a test of an embodiment of the present invention, hereinafter referred to as NAO, for freeze drying of a recombinant *E. coli* strain, the following results were produced:

| corrected cfu/mL | medium LB | Medium LB + Amp | medium BA |
|---|---|---|---|
| before freeze-drying | 3.0E+10 | 3.0E+10 | 2.7E+11 |
| NAO | 3.8E+10 | 1.8E+10 | 1.9E+11 |

-continued

| corrected cfu/mL | medium LB | Medium LB + Amp | medium BA |
|---|---|---|---|
| freeze-dry medium, vial 1 | 2.5E+08 | 2.5E+08 | 1.3E+09 |
| freeze-dry medium, vial 2 | 8.5E+08 | 4.5E+08 | 2.4E+09 |

The NAO stabilizer produces high cfu counts.

Example 2

Stabilizer Optimization and Replacement of Animal Origin Components in Protex-Bb (Feline *Bordetella bronchiseptica*) Vaccine Two 18-month and one accelerated stability study were performed on PROTEX-BB (available from Intervet Inc., hereinafter referred to as the vaccine) vaccine formulated with Animal component stabilizer and NAO stabilizer. The data collected indicates that NAO stabilizer performed at least as well (even better on some occasions) as animal component stabilizer in these studies. An expiration date projection showed that both NAO and animal component stabilized vaccines could be reasonably expected to pass the minimum titer test at least 36 months post-production.

Introduction

This report focuses on the long-term and accelerated stability testing of the vaccine formulated with NAO, stabilizer.

Materials and Methods

Labconco freeze-dryer
3 ml Vials
13 mm lyo stoppers
Bulk components for candidate stabilizers
1 N NaOH
1 N HCl
pH meter
Autoclave
Stir/Hot plate
PPLO solvens
Centrifuge
Blood agar plates
Microtiter pipette
Disposable plate spreaders
Snap Cap Tubes
Incubator (37° C. w/humidity)
0.85% NaCl solution
Sterile WFI
Lyo trays
Matrix automatic pipette
Plate turntable
X+2 Bb 042501 seed
TSB 1. 250 ml TSB was inoculated at 0.1% with study seed and grown overnight at 37° C. with agitation.
2. Bb culture was centrifuged at 3500 rpm for 35 minutes and suspended in a volume of PPLO to facilitate a 6-10× concentrate.
3. Stabilizers were prepared and heated to no more than 80° C. to aid dissolution
4. pH was adjusted to 7.4 with 1 N NaOH and/or 1N HCl.
5. Stabilizer candidates were autoclaved for 30 minutes and filled with Bb bulk antigen at 25% of 0.6 ml fill. Formulations were freeze-dried in the Labconco freeze-dryer. See Table below for cycle.

6. Freeze-dried cakes were observed for cosmetic appearance.

| Labconco Freeze-Dryer Cycle | | | |
|---|---|---|---|
| Segment | Ramp | Temp | Hold |
| 1 | 5° C./min | −34° C. | 3 hours |
| 2 | 5° C./min | −34° C. | 9 hours |
| 3 | 0.05° C./min | 20° C. | 10 min |
| 4 | 5° C./min | 20° C. | 6 hours |
| 5 | 5° C./min | 4° C. | Indefinite |

Discussion

Figure 2:
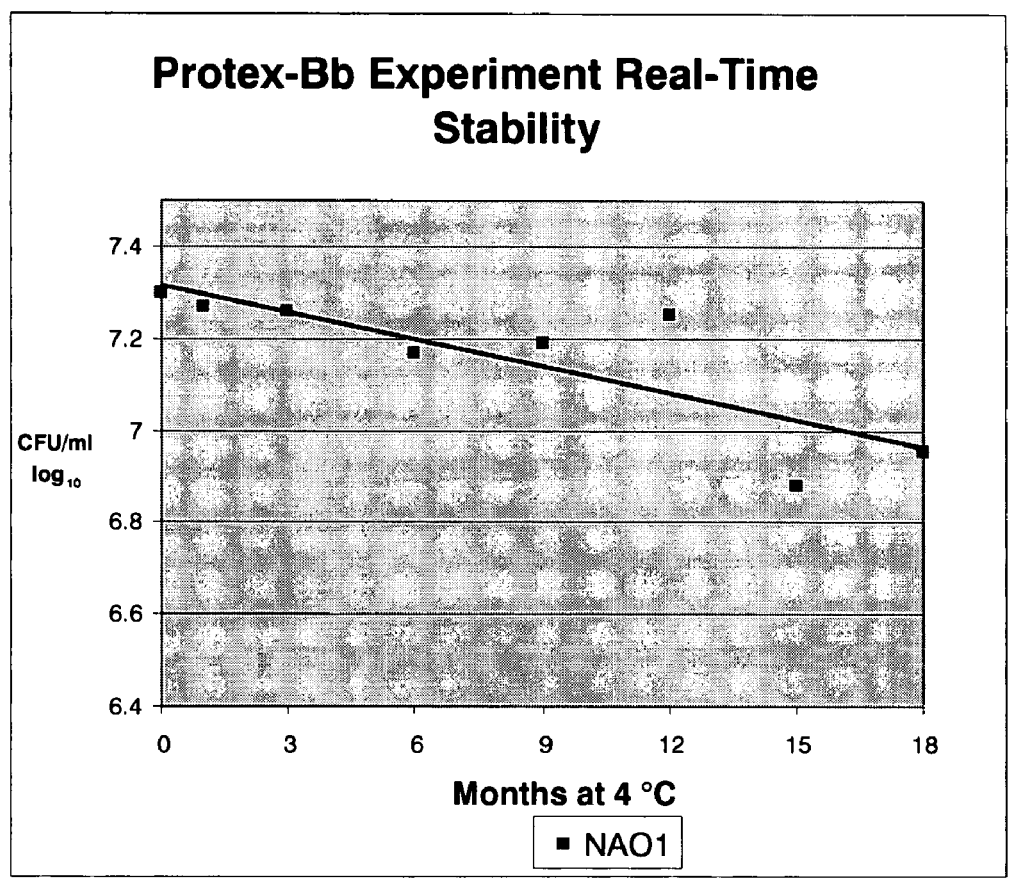
FIG. 2 is an illustration of an alternate lyophilization study of an NAO stabilized vaccine compared to an animal origin component stabilized vaccine titrated over the course of 18 months.

FIGS. 1 and 2 display the results from two lyophilization studies of the vaccine titrated over the course of 18 months. Vaccine containing NAO and animal component stabilizers were freeze-dried and held at 4° C. with titrations performed at 3 month intervals. In both graphs NAO stabilizer shows titer drops comparable to that of animal component stabilizer. Note the narrowness of the scale on the Y-axis in the graph.

Figure 3:
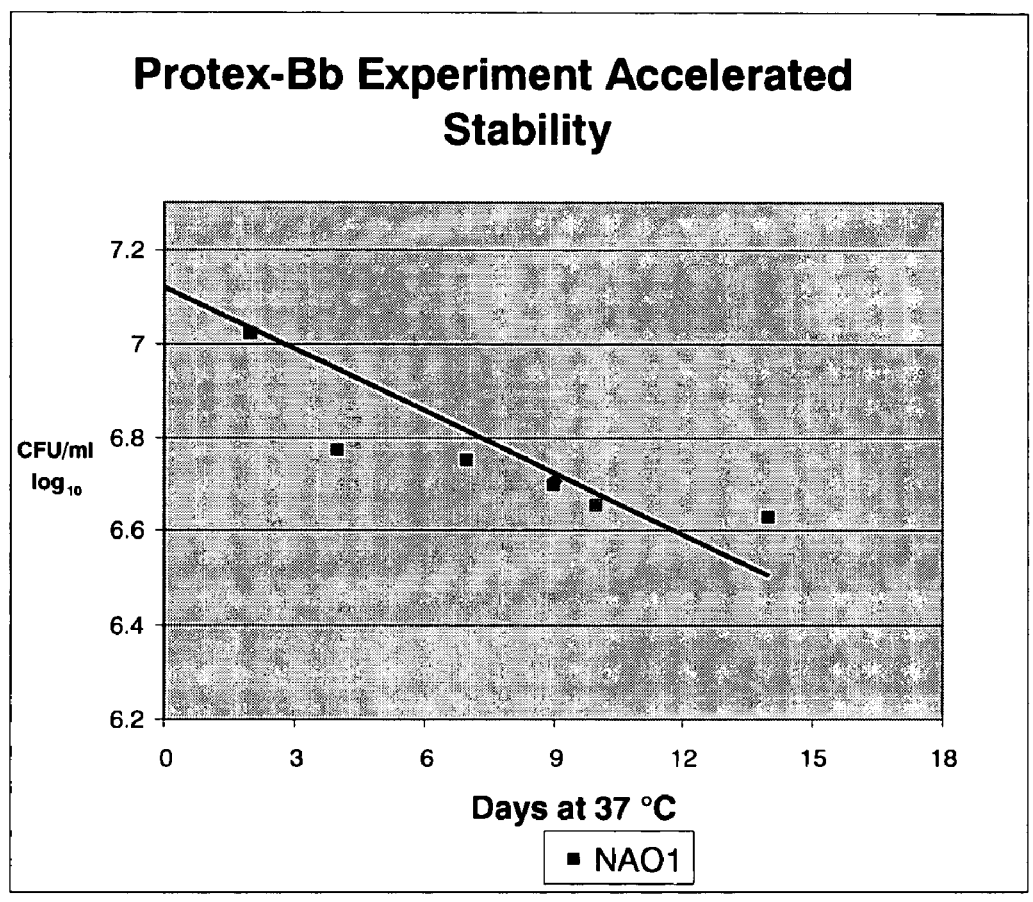
FIG. 3 is an illustration of an alternate lyophilization study of an NAO stabilized vaccine compared to an animal origin component stabilized vaccine.

Further evidence of the value of NAO as a stabilizer for the vaccine can be seen in FIG. 3. An accelerated stability was performed on the material generated in experiment 3. Freeze-dried vials of vaccine were stored at 37° C. for 14 days with titrations performed every 2 to 3 days. The NAO stabilized vaccines are predicted to pass the minimum titer at 3 years on the shelf.

The data presented in this specification supports the idea that animal component stabilizer could be replaced with NAO stabilizer and that this change would not negatively impact freeze-drying loss, stability, cost of goods or shelf life.

Example 3

Stabilizer Formulation and Replacement of Animal Origin Components in PROTEX BB (Feline *Bordetella bronchiseptica*) Vaccine An objective of this example was to design stabilizer formulations free of animal origin components for use in a vaccine composition that show titers upon lyophilization that are equal to or greater than product formulated with the animal component prior art stabilizer. Another objective was to obtain a stabilizer formulation that is protein-free to help reduce site reactions in parenteral use vaccines.

Experimental Design

Each of the candidate stabilizers studied were formulated with the use of bulking agents, lyoprotectants (proteins and sugars) and a buffer in mind. Wherever possible, replacement of animal origin components was investigated.

Eight studies were performed comparing experimental PROTEX-BB (Feline *Bordetella bronchiseptica* Vaccine) vaccine formulations to an actual PROTEX-BB (Feline *Bordetella bronchiseptica* Vaccine) formulation containing animal component stabilizer. (The vaccine is available from Intervet Inc.). A sample with no stabilizer was also included. Candidate and control groups were formulated and freeze-dried. Titrations before and after lyophilization were performed to determine the lyoprotectant activity of the candidate stabilizers when compared to animal component stabilizer and the negative control.

Materials and Methods

Freeze dryer
3 ml Vials
13 mm lyo stoppers
Bulk components of candidate stabilizers
1 N NaOH
1 N HCl
pH meter
Autoclave
Stir/Hot plate
filler
Centrifuge
Blood agar plates
Microtiter pipette
Disposable plate spreaders
Snap cap tubes
Incubator (37° C. w/humidity)
0.85% NaCl solution
Sterile WFI
Lyo trays
Matrix multi-channel pipette
TSB
PROTEX-BB (Feline *Bordetella bronchiseptica* Vaccine) study seed 500 ml of TSB was inoculated at 0.1% with production seed and grown overnight at 37° C. with agitation. The study seed was then formulated with 30% glycerol and frozen at −70° C. for storage.

1. 500 ml TSB was inoculated at 0.1% with the Bb study seed and grown overnight at 37° C. with agitation.
2. PROTEX-BB (Feline *Bordetella bronchiseptica* Vaccine) culture was centrifuged at 3000 rpm for 20 minutes and re-suspended in an equivalent volume of saline solution. This suspension was used in the final formulations of candidate stabilizers.
3. Candidate stabilizers were prepared in R&D and heated to no more than 80° C. to aid dissolution.
4. pH was adjusted to 7.4 with 1 N NaOH and/or 1N HCl.
5. Stabilizer candidates were autoclaved for 30 minutes and formulated with Bb antigen. Stabilized antigens were freeze-dried in either the Usifroid freeze-dryer or the Labconco freeze-dryer.
6. Freeze-dried cakes were observed for cosmetic appearance. Before and after lyophilization, titrations were performed:

A pilot titration was run on each group of samples to determine the dilution at which plates could be read.

Results and Discussion

TABLE 1

| Stabilizer | | Avg % loss |
|---|---|---|
| Experiment 8 Group A | | 22.65% |
| WFI | Qs to 1 L | |
| Sucrose | 85.7 g/L | |
| Lactose | 85.7 g/L | |
| Sorbitol | 85.7 g/L | |
| Na2HPO4 | 0.3 g/L | |
| Dextran 167 | 57.17 g/L | |
| Experiment 8 Group B | | 35.57% |
| WFI | Qs to 1 L | |
| Na2HPO4 | 0.5 g/L | |
| Trehalose | 100 g/L | |
| Peptone | 100 g/L | |
| Dextran 167 | 100 g/L | |

TABLE 1-continued

| Stabilizer | | Avg % loss |
|---|---|---|
| Experiment 8 Group C | | 43.44% |
| WFI | Qs to 1 L | |
| Na2HPO4 | 0.5 g/L | |
| Trehalose | 100 g/L | |
| Dextran 167 | 150 g/L | |
| Negative Control | | 79.97% |

All three of these groups contain no animal origin components and Groups A and C contain no protein at all. Group B does contain protein but it is soy in origin. This study has demonstrated that NAO stabilizers can produce lyophilized product cakes that are both acceptable in percentage loss of titer and cake appeal.

Example 4

Three experiments were conducted in order to optimize the lyophilization of a West Nile Chimera virus. The experiments included the identification of a stabilizer and the development of an appropriate freeze-drying cycle.

It was found that the NAO stabilizers performed better, or, as well as the other stabilizers, showing virtually no loss of titer upon freeze-drying. Various embodiments of the NAO stabilizer were used at 25% of the final formulation volume and together with a 27-hour freeze-drying cycle produced a light pink colored cake with excellent eye appeal.

Further, another embodiment comprised a protein free vaccine candidate.

Materials and Methods
Freeze-dryer
3 ml Vials
13 mm fluted lyo stoppers
Bulk components for candidate stabilizers (Formulations Section)
1 N NaOH or 1 N HCl
pH meter
Autoclave
Balance
Formulation vessels
Magnetic stir bars
Stir/Hot plate
Lyophilization trays
Crimper
13 mm caps
filler ChimericWN bulk antigen
1. Prepare stabilizers according to formulation sheet. See Formulations Section. Heat (to no more than 80° C.) as necessary to aid dissolution.
2. Adjust pH to 7.0 with 1 N NaOH and/or 1N HCl.
3. Autoclave stabilizers for 20 minutes at 121° C.
4. Formulate each experimental group with stabilizer, WN Chimera bulk antigen and filler as is common in the art.
5. Fill vials with 0.5 ml of formulation.
6. Insert stoppers into vials to allow for water vapor to escape during freeze-drying. Load into freeze dryer and start cycle, as is common in the art.
7. At the end of the cycle, stopper the vials and unload. Cap vials and store at 4° C.
8. Observe freeze-dried cakes for cosmetic appearance. Cakes should be rehydrated with 1 ml of WFI prior to titration.

Formulations Section:

| WFI or Equivalent | Qs to 1 L |
|---|---|
| Innovatol PD30 | 100.00 grams/Liter |
| Sorbitol | 100.00 grams/Liter |
| Hy-Soy peptone | 75.00 grams/Liter |
| Citric Acid | 0.44 grams/Liter |
| Dextran | 50.00 grams/Liter |

| Sample one | |
|---|---|
| WFI or Equivalent | Qs to 1 L |
| Sucrose | 85.70 grams/Liter |
| Lactose | 85.70 grams/Liter |
| Sorbitol | 85.70 grams/Liter |
| Citric Acid | 0.44 grams/Liter |
| Dextran | 57.17 grams/Liter |

| Sample two | |
|---|---|
| WFI or Equivalent | Qs to 1 L |
| Sucrose | 85.70 grams/Liter |
| Lactose | 85.70 grams/Liter |
| Sorbitol | 85.70 grams/Liter |
| Peptone (soybean) | 100.00 grams/Liter |
| Citric Acid | 0.44 grams/Liter |
| Dextran | 57.17 grams/Liter |

Results

TABLE 1

WN Chimera Lyophilization Experiment 1 Results

| Group | Stabilizer | Fill Titer | Pre-lyo Titer | *Post-lyo Titer | Loss | % Moisture | Cake |
|---|---|---|---|---|---|---|---|
| A | 25% NAO | 6.5 | 7.2 | 7.2 | 0.0 | 1.8 | Excellent |
| B | Sample one | 6.5 | 7.0 | 6.5 | 0.5 | 2.0 | Excellent |
| C | Sample two | 6.5 | 7.2 | 6.7 | 0.5 | 2.0 | Good, some collapse on bottom |
| D | None | 6.5 | 7.1 | 6.2 | 0.9 | — | Poor |
| E | 12.5% NAO | 6.5 | 7.2 | 7.0 | 0.3 | 2.5 | Excellent |
| F | 25% NAO | 4.5 | 5.3 | 4.0 | 1.3 | — | Excellent |
| G | Sample one | 4.5 | 4.9 | 3.5 | 1.4 | — | Excellent |
| H | Sample two | 4.5 | 4.6 | 3.1 | 1.5 | — | Excellent |

TABLE 1-continued

WN Chimera Lyophilization Experiment 1 Results

| Group | Stabilizer | Fill Titer | Pre-lyo Titer | *Post-lyo Titer | Loss | % Moisture | Cake |
|---|---|---|---|---|---|---|---|
| I | None | 4.5 | 5.2 | 2.7 | 2.5 | — | Poor |
| J | 12.5% NAO | 4.5 | 5.1 | 3.8 | 1.4 | — | Good, cake shrunken slightly |

*Post-lyo titers were adjusted by adding 0.3 log to compensate for dilution upon reconstitution.
Average Loss at 6.5 fill titer 0.6
Average Loss at 4.5 fill titer 1.5

TABLE 2

WN Chimera Lyophilization Experiment 2 Results

| Group | Stabilizer | Fill Titer | Pre-lyo Titer | *Post-lyo Titer | Loss | % Moisture | Cake |
|---|---|---|---|---|---|---|---|
| A | 25% NAO | 6.5 | 7.0 | 7.2 | −0.2 | 1.2 | Excellent |
| B | Sample one | 6.5 | 7.0 | 6.6 | 0.4 | 1.3 | Excellent |
| C | Sample two | 6.5 | 6.9 | 6.8 | 0.1 | 1.7 | Excellent |
| D | None | 6.5 | 7.5 | 6.9 | 0.6 | — | Poor |

*Post-lyo titers were adjusted by adding 0.3 log to compensate for dilution upon reconstitution.

TABLE 3

YF-WN Chimera Lyophilization Experiment 3 Results

| Group | Stabilizer | Fill Titer | Pre-lyo Titer | *Post-lyo Titer | Loss | % Moisture | Cake |
|---|---|---|---|---|---|---|---|
| A | 25% NAO | 6.5 | 7.1 | 7.1 | 0.0 | — | Excellent |
| B | Sample one | 6.5 | 7.1 | 6.0 | 1.1 | — | Excellent |
| C | Sample two | 6.5 | 7.0 | 6.4 | 0.6 | — | Excellent |
| D | None | 6.5 | 6.8 | 6.5 | 0.3 | — | Poor |

*Post-lyo titers were adjusted by adding 0.3 log to compensate for dilution upon reconstitution.

TABLE 4

WN Chimera Lyophilization Experiment Average Results

| Group | Stabilizer | Fill Titer | Pre-lyo Titer | Post-lyo Titer | Loss | % Moisture | Cake |
|---|---|---|---|---|---|---|---|
| A | 25% NAO | 6.5 | 7.1 | 7.2 | −0.1 | 1.5 | Excellent |
| B | Sample 1 | 6.5 | 7.0 | 6.5 | 0.6 | 1.7 | Excellent |
| C | Sample 2 | 6.5 | 7.1 | 6.7 | 0.4 | 1.9 | Excellent |
| D | None | 6.5 | 7.2 | 6.6 | 0.6 | — | Poor |

Discussion

Table 1 displays the data recorded from experiment 1. Fourteen groups were included for study with half of them filled at 6.5 $\log_{10}$/dose (A-E), and the other half filled at 4.5 $\log_{10}$/dose (F-J). Each half was identical to the other in their stabilizers. Groups A and F with 25% NAO stabilizer and so on. The stabilizer used in group B was non-protein NAO and group C contained another form of NAO using three carbohydrates instead of two. Group D contained no stabilizer and was useful in detection of virucidal activity.

The experiment was freeze-dried using a 31-hour cycle which produced acceptable cakes in most all the groups containing 25% stabilizer. Cakes from groups which contained 12.5% stabilizer were less attractive and overall showed higher titer losses. Based on this information, it was decided to pursue a formulation using the higher stabilizer levels.

Regarding titer losses, NAO stabilizer performed better than all other stabilizers at a fill titer of 6.5 $\log_{10}$/ds. Animal component stabilizer performed the best at 4.5 $\log_{10}$/ds although obvious virucidal activity can be seen when the pre-lyophilization results from the animal component stabilizer containing groups are compared with groups containing no stabilizer. Other NAO stabilizers performed fairly well at 6.5 as well. Average losses at the fill titer of 6.5 (average loss 0.6) were much better than those at 4.5 (average loss 1.5).

Tables 2 and 3 display the data generated from lyophilization experiments 2 and 3. There were fewer groups tested in each study since the groups formulated with fill titers of 4.5 log$_{10}$/ds and 12.5% stabilizer had been removed.

Titer results from experiments 2 and 3 were in-line with the conclusion that NAO stabilizer out-performed all other groups losing virtually no titer.

Table 4 displays the average results from the groups common to all three lyophilization experiments and the blank (groups A-D). The results indicate that the NAO stabilizers are an adequate choice for a WN chimera vaccine and are superior from a titer loss viewpoint to the prior art animal origin stabilizer.

Further studies (results not shown) have illustrated that the NAO stabilizers have produced no site or systemic reactions when tested with other stabilizers in an equine study, feline and canine animal model.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims. Such further and other embodiments are contemplated whereby additions of an acid and/or a base may be made to the fermentation. Further, all patents mentioned herein are hereby incorporated by reference.

What is claimed is:

1. A process for producing a stabilized feline *Bordetella bronchiseptica* vaccine composition, wherein the process comprises:
    forming the vaccine composition comprising live, attenuated *Bordetella bronchiseptica* bacteria, a vegetable peptone, a saccharide, a polyhydroxyl alcohol and a buffer, wherein the vaccine composition comprises no animal origin components; and
    lyophilizing said vaccine composition for a period of time, wherein said lyophilization causes a loss of titer that is less than 0.4 log.

2. The process of claim 1, wherein the process further comprises lyophilizing dextran or another polysaccharide with the bacteria.

3. The process of claim 1, wherein the loss of titer from said lyophilization is less than 0.2 log.

4. The process of claim 1, wherein the period of lyophilization is about 31 hours.

5. The process of claim 1, wherein the period of lyophilization is from about 20 to about 140 hours.

6. The process of claim 1, wherein the period of lyophilization is from about 24 to about 120 hours.

* * * * *